Figure 1:
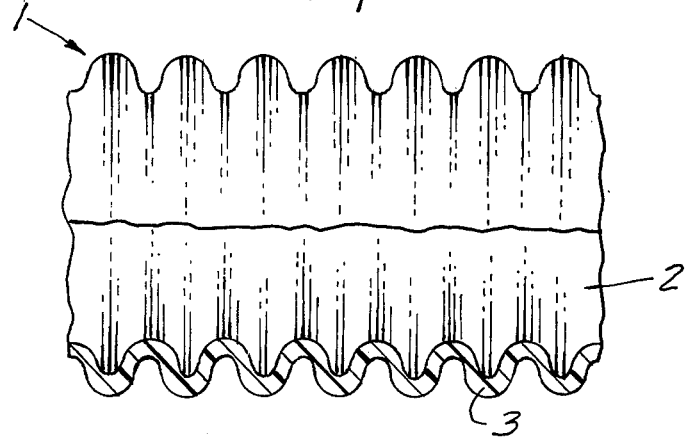

United States Patent [19]

Matson

[11] 4,000,341
[45] Dec. 28, 1976

[54] AUTOCLAVABLE, CORRUGATED, RESPIRATORY CARE TUBING

[75] Inventor: Gale Wendell Matson, Minneapolis, Minn.

[73] Assignee: Minnesota Mining and Manufacturing Company, St. Paul, Minn.

[22] Filed: May 23, 1975

[21] Appl. No.: 580,195

[52] U.S. Cl. .................. 428/36; 428/182; 138/121; 128/145.5; 128/188; 260/876 B; 260/878 R

[51] Int. Cl.² ............... B32B 3/58; A61M 16/00; C08L 53/00; C08L 23/12

[58] Field of Search ............ 428/36, 35, 182; 260/878 R, 878 B, 897 R, 876 R, 876 B; 138/119, 122, 129, 132, DIG. 7, 121; 128/145.5–145.8, 185–188, 142

[56] References Cited

UNITED STATES PATENTS

| | | | |
|---|---|---|---|
| 2,898,941 | 8/1959 | Kilcup | 138/122 X |
| 3,175,999 | 3/1965 | Natta et al. | 260/878 B |
| 3,378,606 | 4/1968 | Kontos | 260/878 B |
| 3,457,920 | 7/1969 | Thompson | 128/145.5 X |
| 3,478,128 | 11/1969 | Hagemeyer, Jr. et al. | 260/878 B |
| 3,823,203 | 7/1974 | DeLaMare | 260/876 B |
| 3,865,776 | 2/1975 | Gergen | 260/876 B |
| 3,894,117 | 7/1975 | Agouri et al. | 260/878 B |

*Primary Examiner*—Philip Dier
*Attorney, Agent, or Firm*—Alexander, Sell, Steldt & DeLaHunt

[57] ABSTRACT

Autoclavable, corrugated, respiratory care tubing comprising thermoplastic material which is aliphatic olefin polymer, aromatic olefin block polymer or mixtures thereof, the material being hydrolytically stable, having a flexular modulus according to A.S.T.M. D-790 of less than 1800 kg/cm², having a Shore A hardness according to A.S.T.M. D-2240 of from 45 to 92 and being substantially dimensionally stable in steam at temperatures of at least about 120° C.

10 Claims, 3 Drawing Figures

AUTOCLAVABLE, CORRUGATED, RESPIRATORY CARE TUBING

This invention relates to corrugated, respiratory care tubing. Specifically, this invention relates to respiratory care tubing which is autoclavable and yet made of thermoplastic material.

Two general types of respiratory care tubing are presently available. These include those that are (1) disposable, or (2) reusable. The disposable type is initially inexpensive, normally used only once, and made of materials such as polyethylene, polyethylene and "Kraton" blends, ethylene/vinyl acetate or polyvinylchloride. This tubing, while disposable, can be expensive in use because it generally must be thrown away after each use. In some cases the tubing is sterilized by the use of ethylene oxide and reused but such reuse is limited.

Reusable tubing is normally made of thermoset resins such as vulcanized elastomers, e.g., silicone rubbers or "Neoprene" rubbers. This type of tubing is expensive because it involves slow and high cost fabrication techniques. The reusable tubing can normally withstand repeated steam sterilization.

A corrugated, respiratory care tubing has been found which can be manufactured inexpensively but which is of the reusable type, i.e., can withstand repeated steam sterilization. It comprises a thermoplastic material selected from the class consisting of aliphatic olefin polymer, aromatic olefin block polymer and mixtures thereof, said material being hydrolytically stable, having a flexular modulus according to A.S.T.M. D-790 of less than 1800 kg/cm$^2$, having a Shore A hardness according to A.S.T.M. D-2240 of from 45 to 92 and being substantially dimensionally stable in steam at temperatures at least about 120° C. As used herein, hydrolytically stable means capable of withstanding at least 20 cycles of 3 minutes duration of contact with steam of at least 120° C. and at least 1 atmosphere (gauge) pressure and retaining at least 90 percent of its initial tensile strength and remaining within the Shore A hardness range of from 45 to 92.

Figure 2:
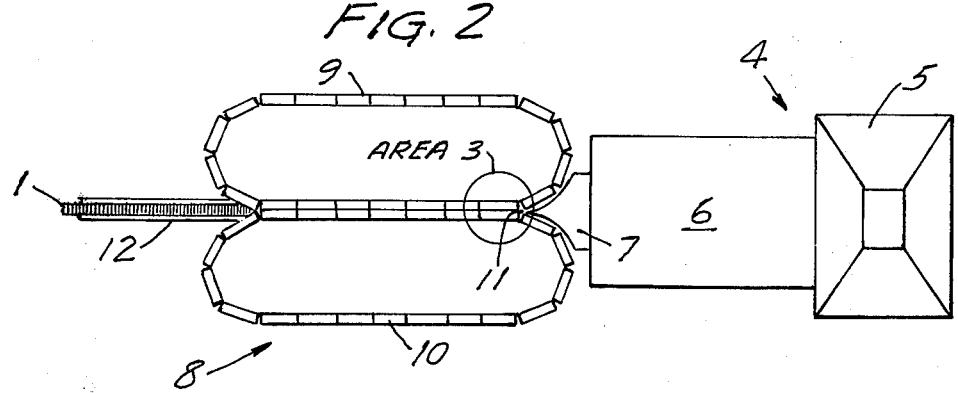
Figure 3:
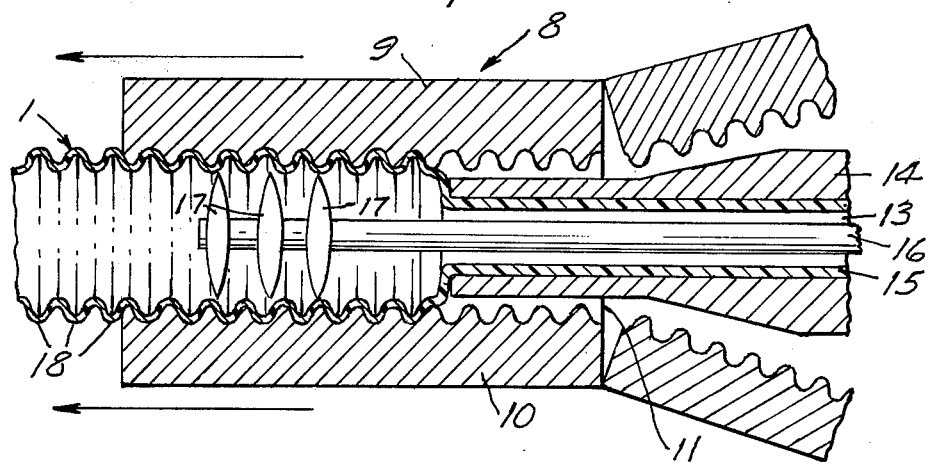

The tubing and method of preparation of the tubing will be described in more detail with reference to the following drawings in which FIG. 1 is an elevation of the tubing of the present invention with parts in section; FIG. 2 is a top schematic view of the extrusion apparatus for making the tubing of the present invention and FIG. 3 is an exploded view of area 3 of FIG. 2 showing in section the portion in the apparatus of FIG. 2 wherein the tubing is formed.

Specifically, in FIG. 1, tubing 1 is shown which comprises void 2 and corrugated walls 3. Corrugated walls 3 comprise thermoplastic aliphatic olefin polymer, aromatic olefin block polymer or mixtures of these polymers. The aliphatic olefin polymers are generally the type of polymers which are made from monomers containing 1 or more ethylenic bonds per monomer unit. One polymer of this type includes isotatic polypropylene in combination with noncrystalline ethylene-propylene random copolymer. This type of polymer incorporates the high temperature characteristics of polypropylene with the elastomeric charcteristics of the ethylene-propylene rubber polymer. These polymers can be produced by means known to the art such as described in U.S. Pat. Nos. 3,175,999 and 3,378,606. Particularly useful thermoplastic materials can be produced by blending of certain rubbers of the ethylene-propylene type with a polyolefin resin, e.g., isotactic polypropylene as described in U.S. Pat. No. 3,835,201. Nonisotatic polypropylene can also be included in such materials. Examples of preferred materials of this type are Uniroyal TPR thermoplastic rubbers, Uniroyal, Inc., Naugatuck, Connecticut, particularly TPR 1600 and 1900. A mixture of from 50 to 90 percent by weight TPR 1600 and from 10 to 50 percent by weight TPR 1900, more preferably about 75 percent by weight TPR 1600 and about 25 percent by weight TPR 1900 is preferred. Various other aliphatic olefin polymers of the above types and mixtures of the above with polyolefins, e.g., polypropylene can also be used as long as they have the stability characteristics, flexular modulus and Shore A hardness set forth above.

The aromatic olefin block polymers can also be used in the tubing of the present invention. These polymers are preferably hydrogenated in order to insure their high temperature properties. Normally, these would be used in a mixture with aliphatic olefin polymers such as those noted above or, for example, polypropylene. The preferred aromatic olefin block polymers are those which are styrene/isoprene/styrene wherein the isoprene portion is hydrogenated and the polymer contains about 16 percent by weight styrene. These type polymers are produced by means known to the art as described in U.S. Pat. No. 3,265,765 and are available from Shell Oil Company, Houston, Texas, under the trademark Kraton. A preferred Kraton is Kraton G-2705 thermoplastic rubber. A preferred mixture is one which comprises 10 to 20 percent by weight polypropylene and 80 to 90 percent by weight Kraton G-2705 thermoplastic rubber.

As noted, the tubing wall material can be one or a mixture of various thermoplastic materials. The thermoplastic material can contain other ingredients which do not prevent the advantages of the invention from being realized, i.e., which do not change the material so that it does not have the physical characteristics discussed in detail below. Examples of useful inclusions are lubricants, fillers such as carbon black which will impart electrical conductivity to the tubing, radioopaque filler such as barium sulfate and colorants.

A preferred tubing is one which is translucent so that liquid build-up in the tubing can be seen through the walls of the tubing. The aforesaid liquid build-up is caused by condensation in the tubing when the tubing is being utilized with a humidifier. The water should be visible through the tubing from a distance of at least three meters.

Carbon black or graphite are often included in tubing used in anesthesia because in those uses the tubing generally must be electrically conductive. The tubing in that instance will be opaque.

The thermoplastic material has a flexular modulus less than 1800 kg/cm$^2$. The preferred flexular modulus is between 700 and 1400 kg/cm$^2$. The Shore A hardness of the thermoplastic material is from 45 to 92, preferably 45 to 80. These measurements are the modulus and hardness of the mixture if the thermoplastic material is a mixture of polymers.

The thermoplastic material must be substantially dimensionally stable in steam at least about 120° C. and at least 1 atmosphere (gauge) pressure, preferably 135° C. and 2 atmospheres gauge pressure. Normally, in a hospital, steam sterilization is carried out in live steam at from 120° to 135° C. for a period of 15 to 3 minutes.

However, some autoclaves operate at temperatures ranging up to about 145° C. A test for dimensionally stability involves measuring the diameter of unloaded, free tubing both before and after an autoclaving sequence to determine whether the tubing has changed dimensions during autoclaving. The dimensions of the tubing at any one point in the tubing should not have changed by more than 10 percent during autoclaving in steam of at least about 120° C., preferably 135° C., and at least 1 atmosphere gauge pressure, preferably 2 atmospheres gauge pressure for 20, 3 minute cycles.

The tubing of the present invention can also be cold sterilized, i.e., can withstand at least 30 cycles of ethylene oxide gas sterilization exposure and 200 hours of aqueous glutaraldehyde disinfectant exposure.

The tubing of the present invention can withstand the normal stress placed on it due to pulling and tugging by the user of the tubing. One test for such properties, hereinafter referred to as the elongation test, is to stretch a tubing whose length, including cuffs, is 100 cm ± 8 cm to twice its original length ± 2 cm within 5 seconds. The tubing is then placed on a flat surface for 10 minutes and the length measured. After this period, the length should not be greater than 125 percent of the original length.

The tubing of the present invention is kink-resistant without reinforcement from inclusions such as wire spirals. The kink-resistance is obtained by having the tubing corrugated and by using in the walls of the tubing thermoplastic material having the designated flexular modulus and Shore A hardness.

The tubing of the present invention also is light in weight. In use the tubing hangs or is draped from the patient. The tubing can be a source of trauma, particularly, since many patients are in a weakened condition and wear the breathing apparatus for prolonged periods. With some patients the tubing extends from a tracheotube inserted in the patient's neck. The preferred tubing of the present invention weighs, without cuffs, about 90 grams per standard 40 inch by 1 inch (100 cm by 2.5 cm) tubing.

The tubing of the present invention normally has about 39 corrugations per 25 cm. of length, has a maximum outside diameter of about 2.87 cm and a minimum outside diameter of about 2.31 cm and normally has a wall thickness which varies from 0.35 to 1.1 mm.

The respiratory care tubing of the present invention is useful in a variety of life-support breathing systems such as volume ventilation, intermittent positive pressure breathing apparatus and oxygen therapy. The tubing of the present invention is also useful in surgical procedures wherein inhalation anesthesia is used.

The tubing of the present invention is made using the extrusion apparatus shown in FIGS. 2 and 3. The material enters the extrusion apparatus 4 through entry port 5 and is heated to a molten flowable mass in heater/-screw section 6. The extrudate flows through die 7 to rotating die 8 comprising two endless die halves 9 and 10 which meet at point 11 in area 3 which is shown in the exploded view of FIG. 3. The corrugated tubing 1 is continuously emitted from die 8 through channel 12.

The specific preparation of the corrugated tubing will be detailed in reference to FIG. 3. Rotating endless die 8 comprising endless die halves 9 and 10 close at point 11. Die 7 contains opening 13 and walls 14. The molten mass 15 flows along the walls 14 of die 7. Also contained within opening 13 is rod 16 containing baffles 17. Air under pressure flows along rod 16 and is forced outwardly from the center of rotating die 8 by baffles 17 so that thermoplastic material extrudate 15 is blown into grooves 18 of rotating die 8. This causes the tubing 1 to be formed in a corrugated configuration along the inner walls of rotating die 8. The rotating die 8 is cooled by ethylene glycol flowing through the frame for the die (not shown) so that the thermoplastic material 15, when emitted from the die as tubing 1 into channel 12 is self-supporting. This method of manufacturing corrugated tubing is known in the art (U.S. Pat. No. 3,243,850.)

The following examples are meant to illustrate but not limit the present invention. All parts and percentages are by weight unless otherwise specified. In the following examples, the following trademarks are used for brevity. The properties of the materials referred by their trademarks are given below:

| | |
|---|---|
| Kraton G-2705 thermoplastic rubber, Shell Oil Company, Houston, Texas Styrene/hydrogenated isoprene/styrene block polymer containing about 16 percent by weight styrene. | |
| Hardness, Shore A | 52 |
| Tensile Properties, ASTM D-412 | |
| Tensile Strength, psi (lb/in$^2$) | 1,650 (116 kg/cm$^2$) |
| Elongation at break, % | 800 |
| Modulus at 100% estension, psi | 200 (14.06 kg/cm$^2$) |
| Set after break, percent | 55 |
| Tear Strength, psi (ASTM D-624) | 130 (9.1 kg/cm$^2$) |
| Compression Set at 70° C.% (ASTM D-395) | 32 |
| Yerzley Resilience, % (ASTM D-945) | 75 |
| Specific Gravity | 0.90 |
| TPR Thermoplastic rubber 1600, Uniroyal, Inc. Naugatuck, Connecticut Combination of isotatic polypropylene and ethylene-propylene rubber | |
| Specific Gravity (ASTM D-471) | 0.88 |
| Hardness, Shore A (ASTM D-2240) | 65 |
| Tensile Strength, psi (ASTM D-412) | 650 (45.7 kg/cm$^2$) |
| Ultimate Elongation, % (ASTM D-412) | 210 |
| 100% Modulus, psi (ASTM D-412) | 550 (38.7 kg/cm$^2$) |
| Tensile Set at Break, % (ASTM D-412) | 10 |
| Compression Set, (ASTM 395B) After 22 hours % at room temp. | 25 |

-continued

| | |
|---|---|
| After 22 hours % at 159° F. (70° C.) | 45 |
| Torsional Modulus, psi (ASTM D-1053) | 300 |
| | (21.1 kg/cm$^2$) |
| Flex Modulus, psi (ASTM D-790) | 1,500 |
| | (105.5 kg/cm$^2$) |
| Bashore Resilience, % Rebound | 50 |
| Split Tear, psi (ASTM D-470) | 45 |
| | (3.2 kg/cm$^2$) |
| (ASTM D-623) | 140 |
| | (9.8 kg/cm$^2$) |
| TPR Thermoplastic rubber 1900, Uniroyal, Inc., Naugatuck, Connecticut | |
| Combination of isotatic polypropylene and ethylene propylene rubber | |
| Specific Gravity (ASTM D-471) | 0.88 |
| Hardness, Shore A (ASTM D-2240) | 92 |
| Tensile Strength, psi (ASTM D-412) | 1,900 |
| | (133.6 kg/cm$^2$) |
| Ultimate Elongation, % (ASTM D-412) | 250 |
| 100% Modulus, psi (ASTM D-412) | 1,850 |
| | (130 kg/cm$^2$) |
| Tensile Set at Break, % (ASTM D-412) | 50 |
| Compression set (ASTM D-395B) | |
| After 22 hours % at room temp. | 40 |
| After 22 hours % at 158° F. (70° C.) | 70 |
| Torsional Modulus, psi (ASTM D-1053) | 3,000 |
| | (211 kg/cm$^2$) |
| Flex Modulus, psi (ASTM D-790) | 20,000 |
| | (1406 kg/cm$^2$) |
| Bashore Resilience, % Rebound | 45 |
| Split Tear, psi (ASTM D-470) | 100 |
| | (7.03 kg/cm$^2$) |
| (ASTM D-624) | 500 |
| | (35.1 kg/cm$^2$) |
| Tenite polypropylene 4250 G, Eastman Chemical Products, Inc., Kingsport, Tennessee | |
| Flow Rate, g/10 min (ASTM D-1238L) | 18 |
| Density, g/cc (ASTM D-1505) | 0.902 |
| Softening Point, Vicat, ° C. (ASTM D-1525) | 143 |
| Deflection Temperature at 264 psi (18.6 kg/cm$^2$) load, ° C. (ASTM D-648) | 57 |
| Stiffness in Flexure, 10$^3$ kg/cm$^2$ (ASTM D-747) | 10.2 |
| Rockwell Hardness, R scale (ASTM D-785) | 92 |
| Izod Impact Strength, Notched, at 23° C. (73° F), ft-lb/in of notch (ASTM D-256) | 0.5 |
| cm-kg/cm of notch | 2.7 |
| Izod Impact Strength, Unnotched at 23° C. (73° F), ft-lb/in of width (ASTM D-256) | >16 |
| cm-kg/cm of width | >86 |
| Izod Impact Strength, Unnotched, at −18° C (0° F), ft-lb/in of width (ASTM D-256) | 4 |
| cm-kg/cm of width | 21.6 |
| Tensile Strength at Yield, kg/cm$^2$ (ASTM D-638) | 337 |

EXAMPLE I

A corrugated respiratory care tubing was prepared from a mixture of 120 parts of TPR 1600 and 40 parts of TPR 1900. The mixture was extruded through a 2½ inch (6.25 cm) Prodex extruder (Koehring Co., Mt. Gilead, Ohio) wherein the entry to the screw was at 400° F. (204° C), the temperature along the extruder screw varied from 405° F. (207° C) at the beginning to 425° F. (218° C) in the last zone of the screw prior to entry to the die. The die leading to the corrugated tubing endless die was 2½ inch (6.25 cm) at its inlet and ⅞ inch (2.2 cm) at its outlet and was at 350° F. (177° C). The endless die halves were cooled through the use of ethylene glycol which was at a temperature of from 10° to 20° F. (−12° to −6° C). The pressure of the air passing through the die leading to the die halves was 1.36 atmosphere gauge. The screw of the extruder was solid and had a 24:1 length diameter ratio. Screw speed was 50 rpm and take-away speed was 29 ft/min. (8.9 meters/min). The take-away portion of the extruder equipment was manufactured by Rainer Isolierohrfabrik, 8852 Rain Am Lech, Germany. Translucent corrugated respiratory care tubing was produced which had about 2.87 cm outside diameter maximum and a minimum outside diameter of about 2.31 cm. The tubing had about 39 corrugations per 25 cm in length and varied from about 0.60 to 1.1 mm in wall thickness.

Into each end or approximately 100 cm of the tubing was placed a respiratory care tubing cuff made of TPR 1900. Each cuff comprised corrugations having a 1.06 inch (2.7 cm) outside diameter at the maximum and 0.84 inch (2.2 cm) outside diameter at the minimum. The cuff had a 1.12 inch (2.84 cm) outside diameter collar next to the corrugations. A cylindrical portion extended from the collar which has a 0.94 inch (2.4 cm) outside diameter and a 0.87 inch (2.2 cm) inside diameter. The total length of the cuff was 1.31 inch (3.3 cm). Into the cylindrical end of each cuff was placed a stopper. Through one stopper was connected a pressure gauge and through the other was connected a source of pressurized air. The tubing was stretched 5 inches (12.7 cm) beyond its normal relaxed length. The air valve was opened and the pressure in the tubing was increased to 60 cm of water (gauge pressure) within 5 seconds. The valve was closed immediately. The pressure was read 10 seconds later. A reading of less than 45 cm of water represented sufficient leakage to be considered a failure by the tubing. When conducted before and after autoclaving, the test is an indication of the amount of melting, cracking or deformation that occurred in the tubing during autoclaving. A measurement of greater than 45 cm of water represents insufficient cracking, etc. to cause critical leakage, i.e., enough leakage to effect the treatment of the patient when the tubing is being used. This test is hereinafter referred to as the leak test.

Another test, hereinafter the flexibility test, was performed on the prepared tubing. It involved affixing vertically one end of one cuff of the cuffed tubing as described above on the top surface and near the edge of a horizontal support. The tubing was allowed to bend over the edge of the support and hang vertically downward under its own weight. The radius of the curvature of the tubing should be such that no portion of the tubing hangs out a greater distance than 15 cm from the extended vertical line of the closest outside edge of the cuff fixed to the support. The tubing should not kink during the test.

The flexibility, elongation and leak tests were performed on the tubing both before and after 50, 10 minute cycles in an autoclave at 135° C. and 2 atmospheres gauge pressure. The tubing passed all three tests in each instance. The tubing ws also found to be dimensionally and hydrolytically stable during the autoclaving.

The tubing was also exposed to a glutaraldehyde disinfectant, Cidex activated dialdehyde, Arbrook, Inc., Arlington, Texas, for 300 hours. No noticeable changes occurred in the tubing as a result of such exposure.

EXAMPLE II

Corrugated, respiratory care tubing was prepared following the procedure of Example I from a mixture of 65 part TPR 1600 and 19 parts conductive carbon black with an average particle diameter of 30 m$\mu$ and 16 parts Tenite polypropylene 4250 G. The tubing passed the flexibility test set forth in Example 1, had a resistance of 20 to 100 megohmes per 100 cm of tubing, passed the elongation test set forth above, and was autoclaved at 135° C. at 2 atmospheres gauge pressure for 50, 3 minute cycles with no noticeable changes. The tubing had approximately the same dimensions as that of Example I and a wall thickness of from about 0.50 to 0.90 mm.

EXAMPLE III

Following the procedure of Example I, corrugated respiratory care tubing was prepared from a mixture of about 85 percent Kraton GX 7050 (Kraton G 2705) and about 15 percent Tenite polypropylene 4250 G. The tubing passed both the flexibility test and elongation test before autoclaving. The tubing was autoclaved for 50, 3 minute cycles at 135° C. at 2 atmospheres gauge pressure and also ethylene oxide (50 cycles) sterilized with no effect on tensile strength and elongation at break. The tubing was dimensionally and hydrolytically stable during autoclaving. The tubing was found not to be as resistant to ultra-violet radiation as the tubing prepared in Example I but was acceptable for use as respiratory tubing. The tubing has approximately the same dimensions as that of Example I and a wall thickness of from about 0.50 to 1 mm.

I claim:

1. Autoclavable corrugated, respiratory care tubing comprising thermoplastic material selected from the class consisting of aliphatic olefin polymer, aromatic olefin block polymer and mixtures thereof, said material being hydrolytically stable, having a flexular modulus according to A.S.T.M. D-790 of less than 1800 kg/cm$^2$, having a Shore A hardness according to A.S.T.M. D-2240 of from 45 to 92 and being substantially dimensionally stable in steam at temperatures of at least about 120° C.

2. The tubing of claim 1 wherein the thermoplastic material is substantially dimensionally stable in steam at temperatures of at least about 135° C.

3. The tubing of claim 2 wherein said thermoplastic material comprises polypropylene and ethylene-propylene polymer.

4. The tubing of claim 3 wherein said polypropylene is isotactic.

5. The tubing of claim 4 wherein said thermoplastic material includes another polyolefin.

6. The tubing of claim 5 wherein said other polyolefin comprises nonisotactic polypropylene.

7. The tubing of claim 2 wherein said thermoplastic material comprises hydrogenated aromatic olefin block polymer.

8. The tubing of claim 7 wherein said thermoplastic material comprises a mixture of aliphatic olefin polymer and hydrogenated styrene/isoprene/styrene block polymer.

9. The tubing of claim 8 wherein said aliphatic olefin polymer comprises polypropylene.

10. The tubing of claim 8 wherein said aliphatic olefin polymer comprises polypropylene and ethylene-propylene polymer.

* * * * *